US005203323A

United States Patent [19]

Tritle

[11] Patent Number: 5,203,323
[45] Date of Patent: Apr. 20, 1993

[54] METERED DOSE INHALER SPACER DEVICE AND ASSOCIATED CLEANING BRUSH

[76] Inventor: Paul E. Tritle, 1460 S. Olympia, Westport, Wash. 98595

[21] Appl. No.: 870,902

[22] Filed: Apr. 20, 1992

Related U.S. Application Data

[63] Continuation-in-part of Ser. No. 724,761, Jul. 2, 1991, abandoned.

[51] Int. Cl.[5] .................... A61M 11/00; A61M 15/00; A61M 16/10

[52] U.S. Cl. .......................... 128/200.23; 128/203.12

[58] Field of Search ...................... 128/200.23, 200.14, 128/200.24, 203.12, 207.14

[56] References Cited

U.S. PATENT DOCUMENTS 4,470,412 9/1984 Nowacki et al. ............... 128/203.12
4,953,545 9/1990 McCarty ....................... 128/200.23

FOREIGN PATENT DOCUMENTS 2110543 6/1983 United Kingdom ........... 128/200.23

*Primary Examiner*—Edgar S. Burr
*Assistant Examiner*—Kimberly L. Asher

[57] ABSTRACT

A tubular expansion chamber with ends each having apertures for inlet and outlet, respectively, for use with a conventional metered-dose inhaler for delivering medicament to a user suffering from asthma or other similar respiratory ailment. The expansion chamber with a metered-dose inhaler inserted in the inlet aperture intercepts the high-velocity discharge of medicament from a pressurized inhaler and produces a concentrated mist for withdrawal by inhalation by the user through the outlet aperture. The expansion chamber is closed on its outlet end by a removable end cap with mouthpiece surrounding and defining the outlet aperture. The constant volume expansion chamber is dimensionally optimized to maximize medicament concentration in a mist of small particles, able to be substantially withdrawn by a asthmatic user in a short, quick breath characteristic of persons with respiratory ailments such as asthma or chronic bronchitis. The dimensional parameters of the chamber are maximized to produce a maximum concentration of medicament mist while neutralizing the high velocity of the inhaler discharge. The expansion chamber is reusable indefinitely in part because it is cleaned after first removing the end cap by a provided brush designed to match the internal dimensions of the chamber and apertures.

5 Claims, 3 Drawing Sheets

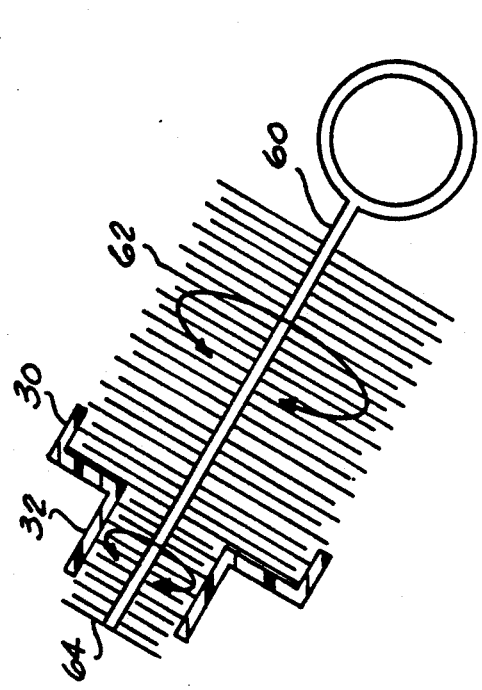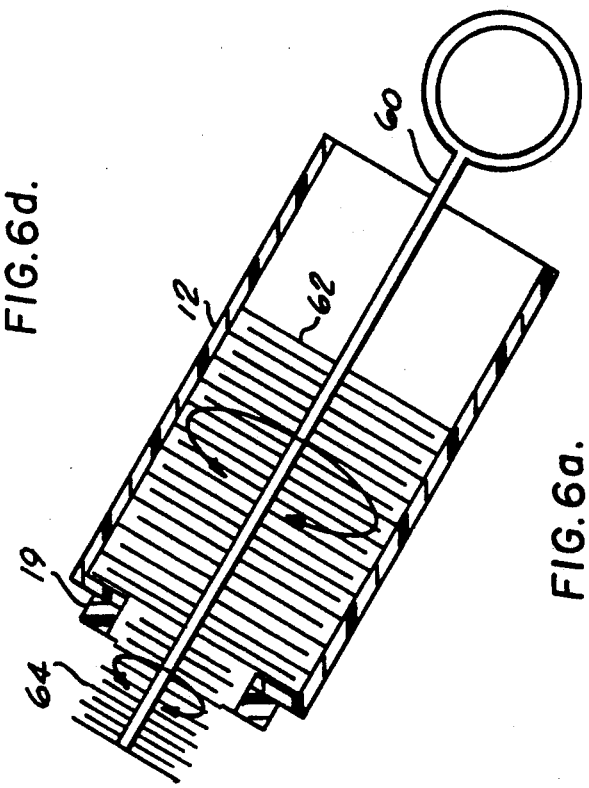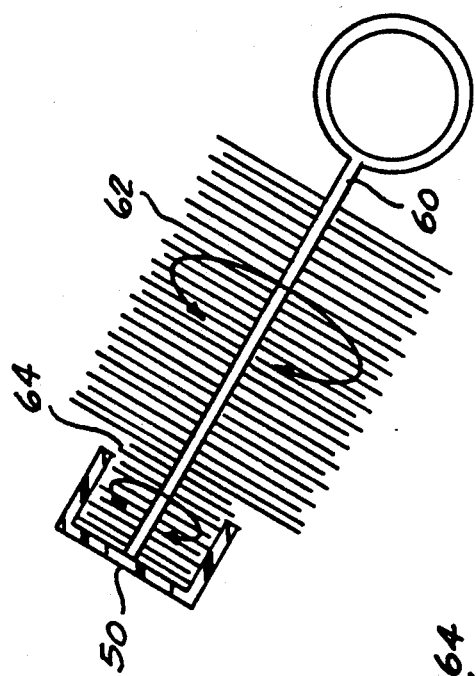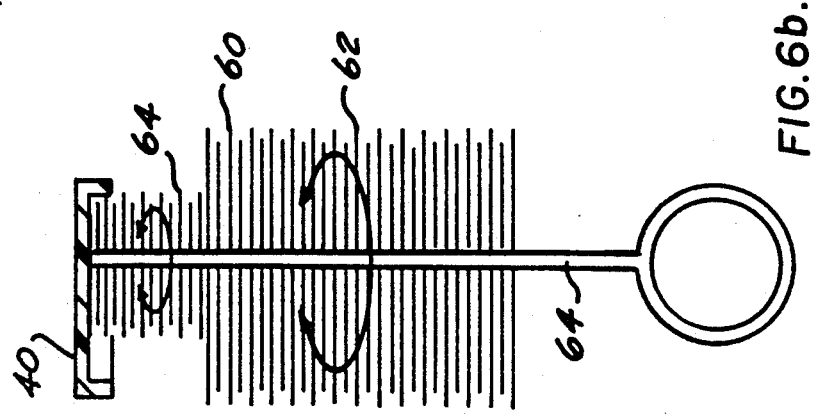

METERED DOSE INHALER SPACER DEVICE AND ASSOCIATED CLEANING BRUSH

This is a continuation-in-part of Ser. No. 07/724,761, now abandoned, filed in the United States on Jul. 2, 1991.

This invention relates to metered dose inhalers which deliver an amount of medicament to a patient's mouth for inhalation into the lungs. More particularly, it relates to a sealed expansion chamber designed to receive a medicament from a pressurized metered dose inhaler in which chamber a mist of medicament is formed which is then inhaled by the patient.

BACKGROUND OF THE INVENTION

Metered dose inhalers are known which deliver a measured amount of a therapeutic drug for treating patients with respiratory ailments. Optimum application occurs when the patient inhales a mist of the medicating drug into lung bronchia and bronchiole. The patient is instructed to place his lips around the mouthpiece of the inhaler and release a charge of medicament into his mouth. However, the medicament is pressurized in the inhalers and is discharged in a high velocity stream that impacts the patient's oropharynx rather than developing a mist that the patient can inhale into his lungs. Unfortunately, the sensation derived from the stream impacting the oropharynx may erroneously convince the patient that the required amount of medicament has been inhaled. As a result, the respiratory ailment remains relatively untreated. In addition, the impact of some drugs on throat tissue can cause undesirable side effects.

Current inhalation techniques teach that a slow, deep inhale is needed to maximize the amount of medicament deposited to a patient's bronchia and bronchiole. However, a patient suffering from a respiratory ailment such as asthma generally suffers from a reduced inhalation capacity—he has great difficulty in taking a slow breath and generally cannot take a deep breath. The breathing technique of the asthmatic patient better approximates a pant of several quick and shallow breaths. Hence, the need exists for a device which allows a respiratory patient to inhale the prescribed medicament during one of these short breaths.

Patients with severe asthma or chronic bronchitis are often instructed to apply their inhaler medication 2 to 5 times daily. Because the medication must be uncontaminated, the inhaler and any inhaler accessory devices must be clean. This requires either disposable devices or ability to clean the devices if they are to be reused.

It is known in the art to have chambers that receive discharge from an inhaler of pressurized medicament from which the patient inhales his medication. Nowacki, U.S. Pat. No. 4,470,412, discloses an inhalation valve in an expansion chamber for simplifying patient inhalation and improving mist formation. The inhalation valve includes a flexible diaphragm member and a support structure positioned upstream of the diaphragm thereby preventing backflow of fluid. The chamber also includes vent holes which allow ambient air into the chamber. Similarly, Hansen, U.S. Pat. No. 3,897,779, teaches a metered dose inhaler with a chamber having vent holes located near the upstream end o fan expansion chamber. Also, McCarty, U.S. Pat. No. 4,953,545, discloses a tapered chamber in combination with a mouthpiece offset from its chamber longitudinal axis to promote swirling within the chamber thereby causing large droplets to precipitate out of the mist before inhalation by the patient. None of these disclosures describe an easily cleaned, reusable expansion chamber in which a medicament mist can be formed and withdrawn by an asthmatic user in a short, quick breath.

It is therefore an object of this invention to provide a substantially sealed, constant-volume expansion chamber with unrestricted fluid flow therethrough for use in combination with a metered-dosage inhaler for delivering a medicament mist to a user's lungs. A further object is that dimensional parameters of the chamber be optimized to maximize the concentration of the medicament mist in the chamber. Another object is to provide an expansion chamber that allows the medicament mist to be substantially withdrawn during a single short breath characteristic of asthmatic users. A final object is that the expansion chamber be reusable and thus can be easily cleaned.

SUMMARY OF THE INVENTION

An expansion chamber is described that is used in combination with a meter-dose inhaler to intercept the high-velocity discharge of medicament from a pressurized inhaler. The expansion chamber has a constant volume with no moving parts or external vents for ease of cleaning, for durability, and for optimizing the mist concentration. The dimensional parameters of the chamber are optimized to produce a maximum concentration of medicament mist while neutralizing the high velocity of the inhaler discharge. The chamber is provided at one end with an inlet aperture into which the inhaler mouthpiece sealingly fits. At the chamber other end is provided an outlet aperture with a chamber mouthpiece over which a user's mouth is closed. The chamber mouthpiece aperture is sized so that substantially all of the medicament mist is uniformally withdrawn during a single short breath a user suffering from a respiratory ailment such as asthma. One end of the chamber is a removable ca to facilitate cleaning. Also to facilitate cleaning, a brush is provided that is formed to the shape of the chamber internal dimensions. Used in combination with the chamber with the cap removed, the chamber is cleaned by the brush, typically with soap and water, and the chamber can be reused indefinitely as very nominal cost. To maintain cleanliness during nonuse, protective cover caps are provided to close the inlet and outlet apertures.

Though expansion chambers for use in combination with conventional metered-dose inhalers are well known and commercially available, previous expansion chambers required long, slow inhalation for successful delivery of medication to the user's lungs, yet an asthma suffer is incapable of such inhalation. The present expansion chamber is specifically designed for use by a user suffering with asthma or a similar respiratory ailment. Though appearing simple in design, the invention discloses a new chamber heretofore unavailable for the asthmatic patient, defining result-effective parameters required to achieve a new expansion chamber that could aid in delivery of medicament to an asthma sufferer. These parameters are experimentally optimized and incorporated in the embodiment presented. Though perhaps deceivingly simple in its resulting design, this chamber nevertheless uniquely provides a major improvement in medicament delivery systems.

The parameters recognized to be result effective are length and volume of the expansion chamber and diameter of the mouthpiece outlet aperture. Length of the chamber is bounded by the need to allow discharged medicament from the inhaler to decelerate in the chamber yet short enough to impact against the chamber at a speed that breaks the medicament into small aerosols, thereby forming an optimum mist.

Length in combination with the chamber diameter defines the chamber volume which is sized to maximize the mist concentration. A volume too large will dilute the mist and will not be withdrawn by a single short asthmatic breath. A volume too small will cause medicament to precipitate out of the mist and rduce medicament delivered. It must also be large enough to approximately match the mist volume that can be inhaled by the intended user so that the medication flows into the lungs during a full, though short breath. The length to diameter ratio must also allow for unrestricted fluid flow in withdrawal from the chamber and minimize the number of reflections within the chamber while minimizing the number of impacts of droplets on the chamber wall which leaves medicament there with each impact. Thus, the chamber volume is optimized to that which an asthmatic-type breath can substantially withdraw, large enough such that the withdrawal extends over the entire breath for optimum delivery to the lungs, maximizing concentration of medicament in the chamber volume when a presently commercially-available, pressurized inhaler discharges into the volume. The mouthpiece aperture is also sized such that substantially all of the volume of the chamber is withdrawn evenly over the short extent of the user's inhalation.

It is clear that the optimum dimensions is dependent in part on the characteristics of the metered-dose inhaler, so if those characteristices were to change then so would the size characteristics of the chamber to maintain the real limitation—a chamber with maximum concentration of medicament with a withdrawal rate such that it can be inhaled by a use in a single, short, "asthmatic" breath. The design results though deceiving in their simplicity, are nevertheless a major improvement in medicament delivery systems.

BRIEF DESCRIPTION OF THE DRAWINGS

FIG. 6a through 6d shows the brush in combination with expansion chamber components during cleaning.

DESCRIPTION OF THE PREFERRED EMBODIMENT

Figure 1:
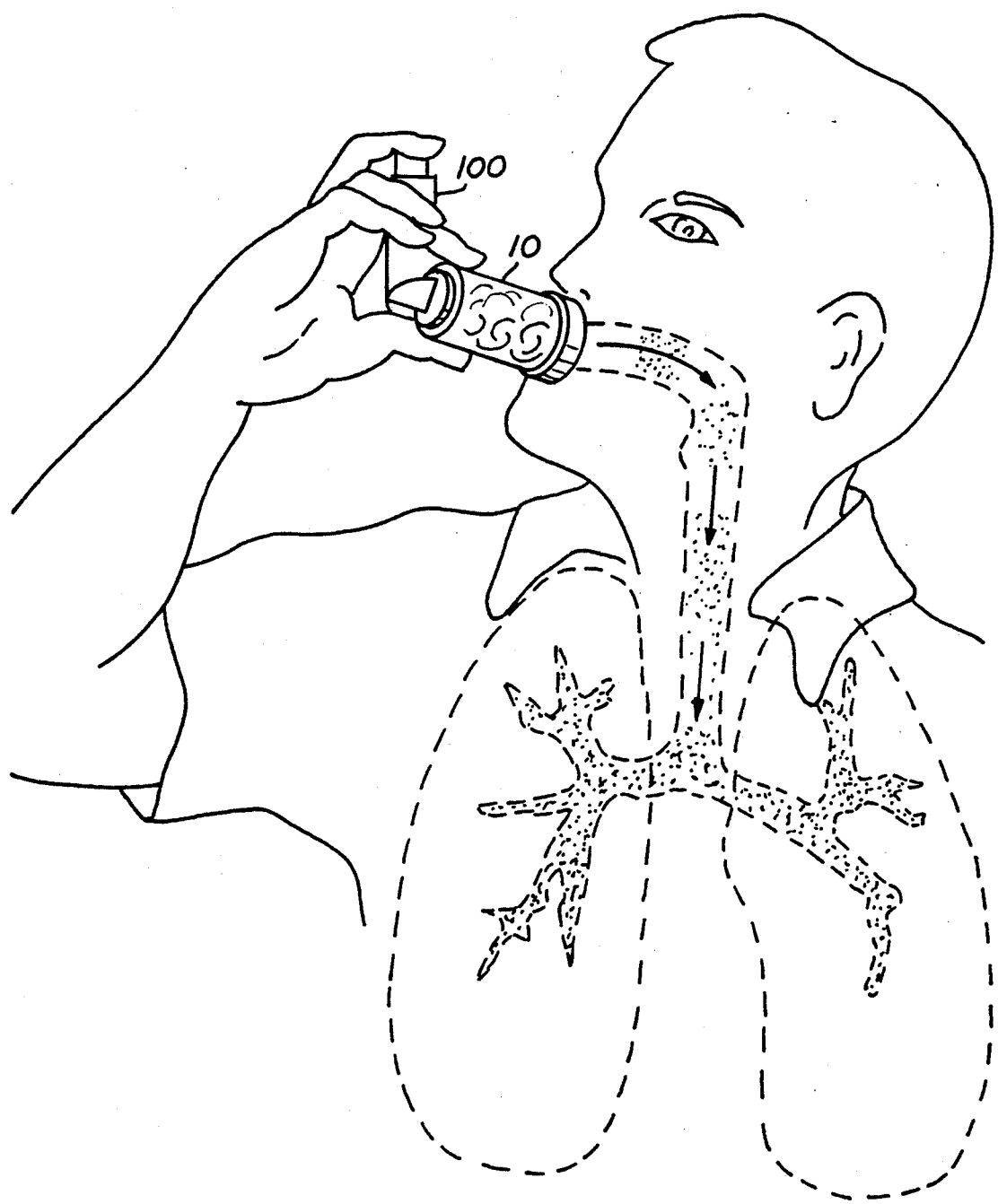
FIG. 1 is a pictorial view of a user administering medication from a metered dose inhaler and the expansion chamber of this invention.
Figure 5:
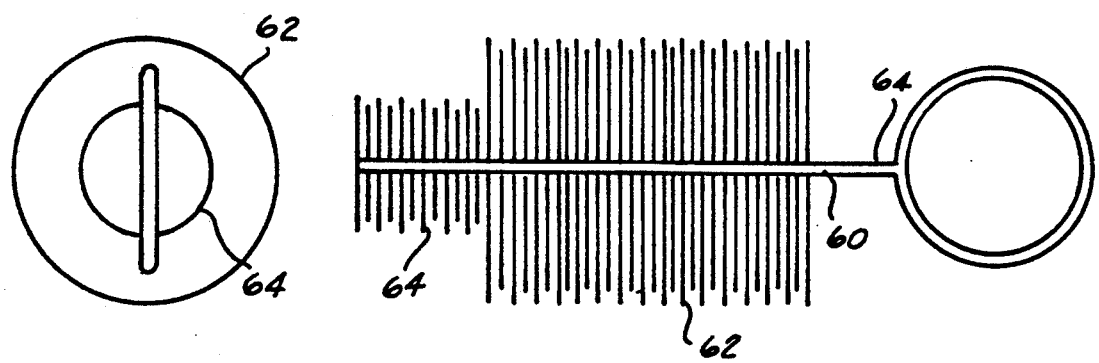
FIG. 5 is a side and end view of the cleaning brush.
Figure 3:
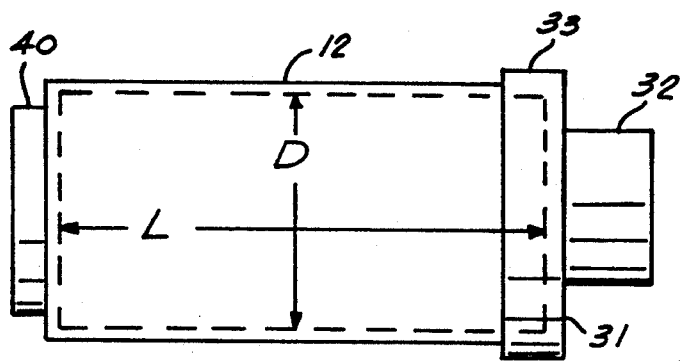
FIG. 3 is a side view of the expansion chamber.
Figure 4:
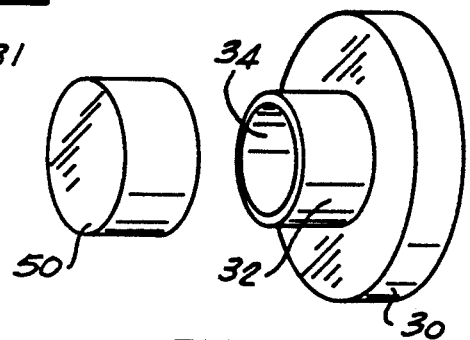
FIG. 4 is an isometric projection view of the outlet end cap with mouthpiece and mouthpiece protection cover cap.
Figure 2:
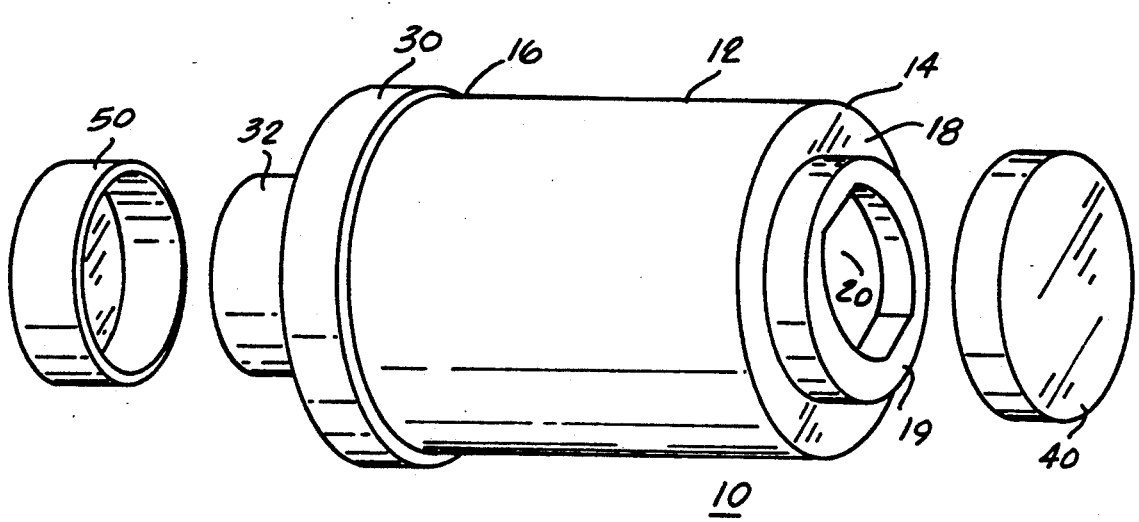
FIG. 2 is an exploded isometric view showing the expansion chamber from its partially closed inlet end, an inlet protective cover cap, an outlet end cap with mouthpiece, and a mouthpiece protective cover cap.

Referring to the figures, the present invention, in its usual configuration, comprises an expansion chamber 10 made of a material impervious to air, such as polypropylene plastic, having a tubular member 12 with a partially closed inlet end 14 and an outlet end 16, a transverse wall member 18 extending radially inwardly from, and formed integral with, the tubular member 12 at its inlet end 14 with an inlet aperture 20 in the transverse wall member 18 forming the partially closed inlet chamber end 14. To strengthen the transverse wall member 18 for receiving a metered dose inhaler, the transverse wall member 18 at the inlet aperture 20 may further comprise inlet aperture collar 19 surrounding and defining the inlet aperture 20 and extending out from the transverse wall member 18. The tubular member 12 is characterized and defined by internal length L and internal diameter D. The inlet aperture 20 is shown to have a generally truncated ovoid shape to interfit and substantially seal a matching mouthpiece of a metered-dose inhaler 100. The chamber outlet end 16 is closed by a removable outlet end cap 30 formed by a transverse wall portion 31 extending radially inwardly from a tubular band 33, sized to fit over the tubular outlet end with a substantial air seal. The outlet end cap 30 further comprises a mouthpiece 32 with an outlet aperture 34 through which a fluid mist can pass out of the expansion chamber 10 and sized such that a user's lips can easily form a sealed connection therewith. Inlet protective cover cap 40, shaped to interfit with the inlet aperture 20, is provided to close the chamber during nonuse. Outlet mouthpiece 32 is also provided with a mouthpiece protective cover cap 50 sized to sealingly fit over the mouthpiece 32, also to close the chamber during nonuse to prevent contamination of the chamber.

The ratio of length L to diameter D of expansion chamber tubular element 12 is optimized at approximately 2:1. The volume of the chamber is optimized at approximately 4.4 cubic inches with internal length L at approximately 2.8 inches and internal diameter D at approximately 1.4 inches.

Withdrawal from the chamber 10 is regulated by the size of the outlet mouthpiece aperture 34 such that over a single short, quick inhalation from a user, such as is typical from a user suffering from asthma or chronic bronchitis, the concentrated medicament mist is substantially withdrawn evenly from the chamber 10 through the outlet mouthpiece aperture 34 and into the users lungs and bronchi and bronchiole. The numeric ratio of chamber volume to mouthpiece aperture diameter Dm that achieves this design parameter is approximately 7:1. Given the chamber volume to be 4.4 cubic inches, the mouthpiece aperture diameter Dm is approximately 0.6 inches, though it was also found that this ratio can vary considerably and still produce effective results.

To achieve a reusable expansion chamber, the chamber must be maintained clean. When used in combination with cleaning brush 60, a user can effectively clean the chamber with soap and water after first removing the outlet end cap 30. The cleaning brush 60 comprises brush bristles on a bristle core 64. For effective cleaning, the brush bristles are sized in two sections with large bristles 62 approximately matching the internal diameter of the chamber tubular member 12 and the outlet end cap 30, oversized by approximately 0.1 inch., followed at the brush end by small bristles 64 matching the internal diameter of the outlet B mouthpiece aperture 34, also oversized by approximately 0.1 inch. The chamber and the outlet mouthpiece are cleaned with soap and water using the appropriate portions of the brush—large bristles for the tubular member and small bristles for the inlet apertures.

The method of using the expansion chamber 10 of this invention can affect the extent of application of medicament to the user's lungs. Optimum delivery of medicament to a user's lungs, bronchi and bronchiole using an inhaler expansion chamber in combination with the user inhaling in short, quick breaths, comprises the steps, after removing the protective cover caps, of first placing a metered-dosage inhaler sealingly in the chamber inlet aperture; producing a mist of medicament with maximum concentration in the chamber by discharging the metered-dose inhaler into the chamber while the user has his mouth over the chamber outlet opening; and then inhaling in a short, quick breath thereby substantially withdrawing the concentrated mist into the user's lungs and bronchi. Techniques have been derived for using the expansion chamber in delivering medicament to the lungs, recognizing the difficulty of the asthmatic user to breathe. One such technique is for the user to discharge the medicament into the chamber and slightly delay inhalation to the end of a "1-2" count. This technique has been found less successful for children, so another equally successful technique is used: after a small number of deliberate breaths, perhaps 3, the user discharges the medicament into the chamber with his mouth closed around the chamber mouthpiece and then inhales the medicament mist from the chamber. The protective cover caps are then replaced after use.

Having described the invention, I claim:

1. A constant-volume, sealed inhaler expansion chamber with unrestricted fluid flow therethrough for use in combination with a metered-dosage inhaler for delivering medicament to a user's lungs, comprising
   a tubular member having a partially closed inlet end sized to sealingly interfit with said metered-dosage inhaler and further having an open outlet end;
   a transverse wall member extending radially inwardly from, and formed integral with, the tubular member at its inlet end with an inlet opening in the transverse wall member forming the partially closed inlet end;
   an outlet end cap having a transverse wall portion extending radially inwardly from a tubular band and having an outlet opening in the end cap, said tubular band sized to sealingly fit over the outlet end of the expansion chamber;
   a mouthpiece with a mouthpiece aperture therethrough through which a fluid mist can pass out of the expansion chamber, the mouthpiece being adapted to sealingly fit integrally with the outlet opening in the end cap and sized such that a user's lips can easily form a sealed connection therewith, and the ratio of chamber volume to mouthpiece aperture diameter is approximately 7 to 1 so that withdrawal from the chamber is regulated such that over a single short, quick inhalation from a user, such as in typical from a user suffering from asthma or chronic bronchitis, the concentrated medicament mist is substantially withdrawn evenly form the chamber through the mouthpiece and into the users lungs an bronchi and bronchiole.

2. The expansion chamber of claim 1 wherein the expansion chamber with tubular member, wall member, and end cap with mouthpiece when used in combination with said inhaler is sized such that ratio of internal length of the chamber to internal diameter of the chamber is approximately 2 to 1.

3. The expansion chamber of claim 1 wherein the volume of the chamber is approximately 4.4 cubic inches.

4. The expansion chamber of claim 1 further comprising a mouthpiece cap sized to snugly fit over the mouthpiece so that mouthpiece aperture is closed by the mouthpiece cap to minimize chamber contamination through the mouthpiece during nonuse.

5. A constant-volume, sealed inhaler expansion chamber with unrestricted fluid flow therethrough for use in combination with a metered-dosage inhaler for delivering medicament to a user's lungs and with a matching brush for cleaning the expansion chamber, comprising
   a tubular member having a partially closed inlet end sized to sealingly interfit with said metered-dosage inhaler and further having an open outlet end;
   a transverse wall member extending radially inwardly from, and formed integral with, the tubular member at its inlet end with an inlet opening in the transverse wall member forming the partially closed inlet end;
   an outlet end cap having a transverse wall portion extending radially inwardly form a tubular band and having an outlet opening in the end cap, said tubular band sized to sealingly fit over the outlet end of the expansion chamber;
   a mouthpiece with a mouthpiece aperture therethrough through which a fluid mist can pass out of the expansion chamber, the mouthpiece being adapted to sealingly fit integrally with the outlet opening in the end cap and sized such that a user's lips can easily form a sealed connection therewith;
   the brush comprising a first set of bristles extending radially outward a distance slightly greater than the inner diameter of the expansion chamber tubular member and outlet end cap, and a second set of bristles at the brush end extending radially outward a distance slightly greater than the inner diameter of the mouthpiece aperture.

* * * * *